United States Patent
Perraud et al.

(10) Patent No.: US 9,387,336 B2
(45) Date of Patent: Jul. 12, 2016

(54) METHOD FOR PRODUCING A HERMETICALLY SEALED CASING INTENDED FOR ENCAPSULATING AN IMPLANTABLE DEVICE, AND CORRESPONDING CASING

(71) Applicant: COMMISSARIAT A L'ENERGIE ATOMIQUE ET AUX ENERGIES ALTERNATIVES, Paris (FR)

(72) Inventors: Simon Perraud, Bandol (FR); Nicolas Karst, Folkling (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 14/674,489

(22) Filed: Mar. 31, 2015

(65) Prior Publication Data

US 2015/0273219 A1 Oct. 1, 2015

(30) Foreign Application Priority Data

Mar. 31, 2014 (FR) ..................................... 14 52790

(51) Int. Cl.

| | |
|---|---|
| *A61N 1/375* | (2006.01) |
| *B23K 1/00* | (2006.01) |
| *B23K 1/18* | (2006.01) |
| *B23K 1/19* | (2006.01) |
| *B23K 26/28* | (2014.01) |
| *B23K 26/32* | (2014.01) |
| *A61N 1/36* | (2006.01) |

(52) U.S. Cl.
CPC .............. *A61N 1/375* (2013.01); *A61N 1/3754* (2013.01); *B23K 1/0008* (2013.01); *B23K 1/18* (2013.01); *B23K 1/19* (2013.01); *B23K 26/28* (2013.01); *B23K 26/32* (2013.01); *A61N 1/3605* (2013.01); *B23K 2203/14* (2013.01); *B23K 2203/18* (2013.01); *B23K 2203/52* (2015.10)

(58) Field of Classification Search
None
See application file for complete search history.

(56) References Cited

U.S. PATENT DOCUMENTS 5,750,926 A 5/1998 Schulman et al.

FOREIGN PATENT DOCUMENTS

| EP | 0 266 210 | 5/1988 |
|---|---|---|
| EP | 1 445 798 | 8/2004 |
| WO | 2006/097842 | 9/2006 |
| WO | 2012/015756 | 2/2012 |
| WO | 2013/099167 | 7/2013 |
| WO | 2013/137214 | 9/2013 |

*Primary Examiner* — Brian T Gedeon
(74) *Attorney, Agent, or Firm* — Clark & Brody

(57) ABSTRACT

Method for producing a hermetically sealed casing, comprising the following steps:
a) supplying a ceramic substrate (20),
b) supplying a metal surround (21) and placing it facing the said substrate (20),
c) forming a first hermetically sealed joint (22) at the interface between the said substrate (20) and the said metal surround (21), in order to assemble them and form an assembly,
d) superposing a cover (23) on the said assembly,
e) forming a second hermetically sealed joint (24) between an upper face of the metal surround (21) which is the opposite face to the said interface, and the cover (23), in order to obtain the said casing,
characterized in that, during step c), the first hermetically sealed joint (22) is formed on a portion of the said interface and in that prior to step c), the method involves an additional step consisting in placing a ceramic surround (25) on the upper face of the metal surround so as to partially cover the said face of the metal surround, the projected surface of the said ceramic surround in a plane of projection covering the projected surface of the said first joint in this same plane of projection.

10 Claims, 3 Drawing Sheets

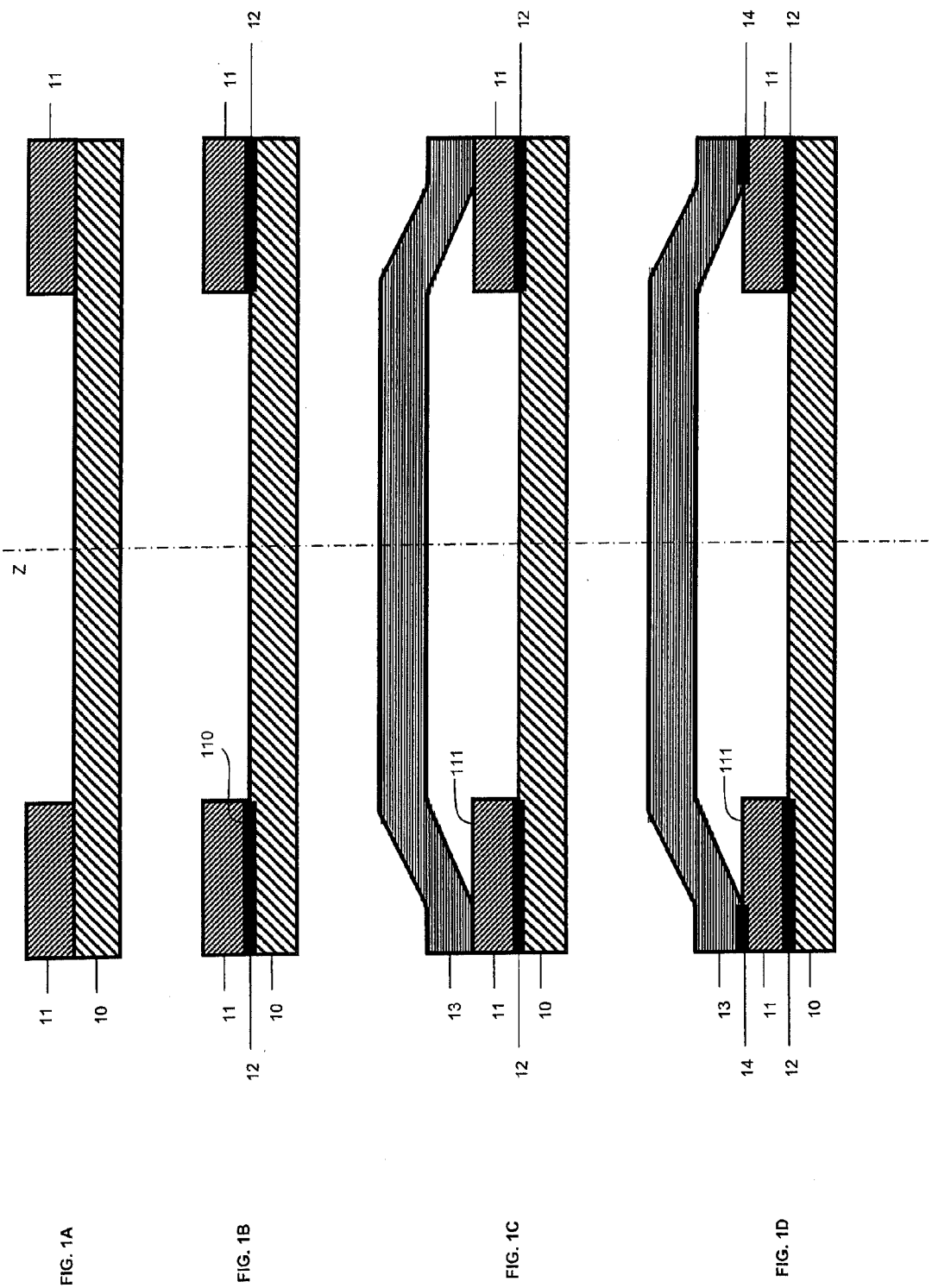

Figure 2A:
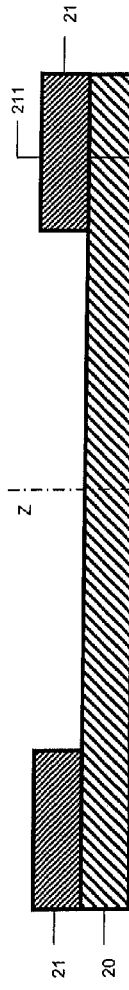

METHOD FOR PRODUCING A HERMETICALLY SEALED CASING INTENDED FOR ENCAPSULATING AN IMPLANTABLE DEVICE, AND CORRESPONDING CASING

The invention relates to a method for producing a hermetically sealed casing notably intended for encapsulating a device and more particularly an implantable medical device.

The invention also relates to such a hermetically sealed casing.

Implantable biomedical devices, such as pacemakers, cardioverter defibrillators, heart monitors, pumps, biomedical sensors or neurostimulation devices, are made up of a battery and of a collection of electronic components which are encapsulated in a biocompatible metal (generally titanium) casing.

In addition to being biocompatible by nature, the casing in which the various components of the device are encapsulated needs to be hermetically sealed in order to avoid any contact between the components and the biological fluids or tissues.

In general, it is desirable for the volume occupied by these devices to be small. In the case of neurostimulators, this means that new implantation sites can be contemplated, getting as close as possible to the sites that are to be electrically stimulated.

In order to do this, various solutions for hermetic and biocompatible encapsulation have been proposed in the literature as alternatives to the titanium casing conventionally used.

Thus the Schulman et al. U.S. Pat. No. 5,750,926 describes a casing that encapsulates the various components required for correct operation of a neurostimulator. It is obtained by fixing a metal cover to an insulating substrate. There are two steps required in order to hermetically seal the casing: the first step is to form a first hermetically sealed joint between a metal surround and the insulating substrate, generally by brazing. The second step creates a second hermetically sealed joint between the metal surround and the metal cover by localized welding and notably by laser welding.

In this casing, it is difficult to use a thin metal surround, for example of less than 1 mm thick.

This is because if a thin metal surround is used, then there are at least two problems that may arise in implementing the method of manufacture:

During the formation of the first hermetically sealed joint by brazing, chemical elements contained in the brazed joint diffuse through the thickness of the metal surround, resulting in undesirable attachment of the metal surround to a holder holding it on the substrate.

When the second hermetically sealed joint is being formed by laser welding, the first hermetically sealed joint may be adversely heat-affected.

It is an object of the invention to further reduce the thickness of the encapsulation cases without compromising the mechanical integrity thereof, notably in order to obtain casings that are mechanically flexible.

This is because such slender and flexible casings are appreciably more comfortable for the patient and make it possible to contemplate implanting them into sites in the human body which are difficult to access with conventional devices. In the case of implantable neurostimulators, they allow implantation as close as possible to the site that is to be electrically stimulated, thereby reducing the risks associated with the breakage of the extension leads and electrode probes.

Thus, the invention relates to a method for producing a hermetically sealed casing, comprising the following steps:

a) supplying a ceramic substrate,
b) supplying a metal surround and placing it facing the said substrate,
c) forming a first hermetically sealed joint at the interface between the said substrate and the said metal surround, in order to assemble them and form an assembly,
d) superposing a cover on the said assembly,
e) forming a second hermetically sealed joint between the face of the metal surround which is the opposite face to the said interface and the cover, in order to obtain the said casing.

According to the invention, during step c), the first hermetically sealed joint is formed on a portion of the interface and the method involves, prior to step c), an additional step consisting in placing a ceramic surround on the opposite face of the metal surround to the said interface so as to partially cover this face, the projected surface of the said ceramic surround in a plane of projection covering the projected surface of the said first joint in this same plane of projection.

With preference, the first hermetically sealed joint formed during step c) is a brazed joint.

In a first alternative form, during step a), a substrate in which a recess is formed may thus be supplied, the brazed joint being incorporated at least partially into the said recess.

In a second alternative form, during step b), a metal surround in which a recess is formed may be supplied, the brazed joint being at least partially incorporated into the said recess.

The invention also relates to a method of encapsulating a device consisting in implementing the method of producing a hermetically sealed casing according to the invention and in mounting at least one component of the said device that is to be encapsulated on the substrate, after step c).

The invention also relates to a hermetically sealed casing comprising:
  a ceramic substrate,
  a metal surround hermetically connected to the substrate by a first joint situated on a portion of the interface between the said substrate and the said surround, and
  a cover hermetically connected to the said metal surround by a second hermetically sealed joint, so as to define a cavity,
characterized in that a ceramic surround is connected to the said metal surround on its face opposite to the said interface, so as to partially cover the said face of the surround, the projected surface of the said ceramic surround in a plane of projection covering the projected surface of the said first joint in this same plane of projection.

In a first alternative form of embodiment of the casing, the ceramic surround is situated on the inside of the cavity.

In a second alternative form of embodiment of the casing, the ceramic surround is situated on the outside of the cavity.

The first hermetically sealed joint is preferably a brazed joint.

In that case, the said substrate and/or the said metal surround advantageously comprises/comprise a recess in which the said brazed joint is at least partially incorporated.

Figure 2B:
Figure 2C:
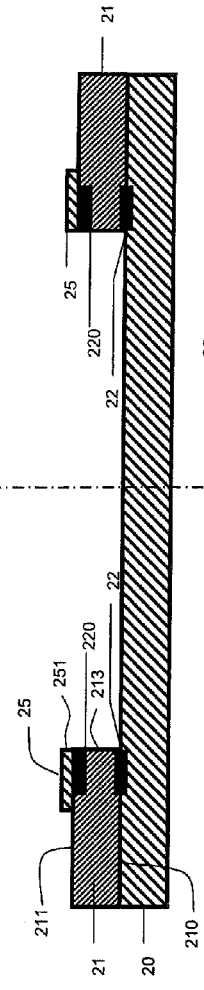
Figure 2D:
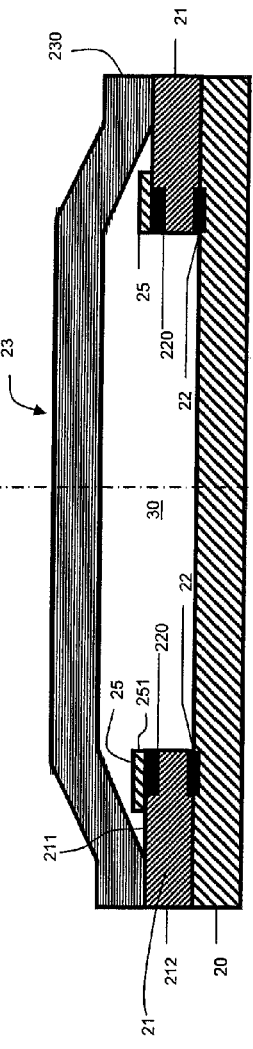
Figure 2E:
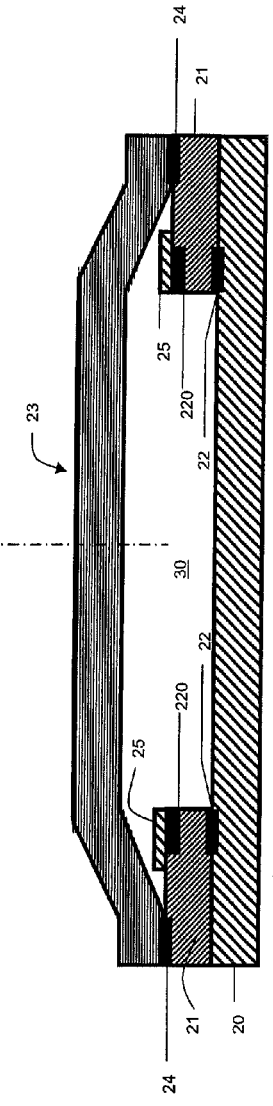
Figure 3A:
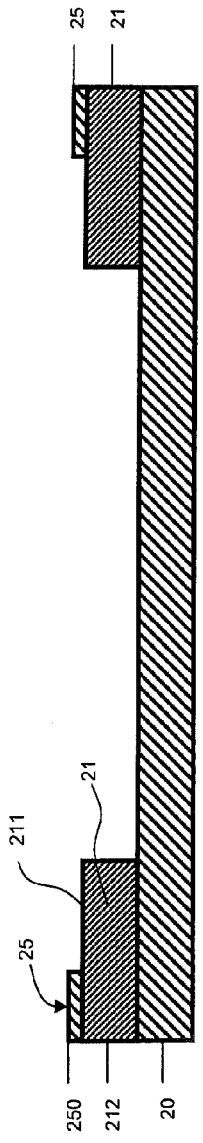
Figure 3B:
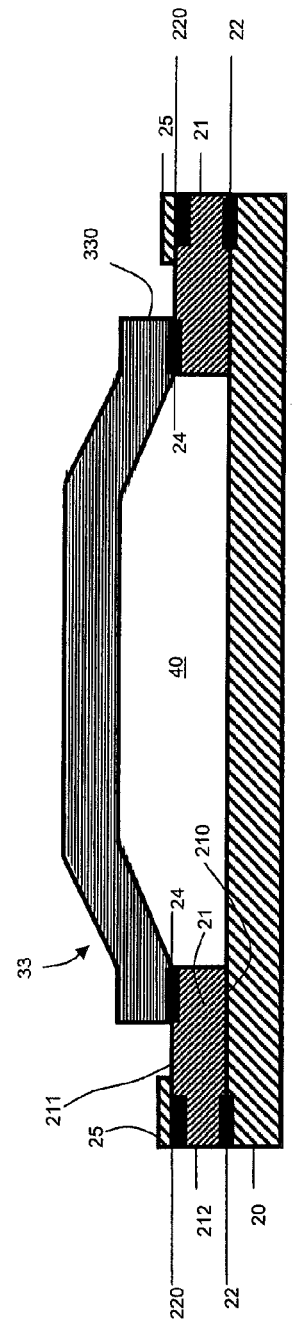

The invention will be better understood, and other objects, advantages and features thereof will become more clearly apparent from reading the following description made with reference to the attached drawings, in which:

FIGS. 1A to 1D are views in section illustrating steps of a method according to the prior art for obtaining a hermetically sealed casing, FIGS. 2A to 2E illustrate the various steps of a method according to the invention for obtaining a hermetically sealed casing, and FIGS. 3A and 3B are views in section illustrating an alternative form of embodiment of the steps of the method which are illustrated in FIGS. 2B and 2E.

The elements which are common to the various figures will be denoted by the same references.

FIG. 1A describes the first two steps of a method according to the prior art, in which steps a ceramic substrate 10 is supplied, with a metal surround 11 placed facing it.

FIG. 1B illustrates a third step of the method, in which step a first hermetically sealed joint 12 is formed at the interface between the metal surround 11 and the substrate 10, or alternatively, between a lower face 110 of the metal surround and the substrate 10.

This first hermetically sealed joint 12 is formed by brazing and allows the substrate and the surround to be assembled.

FIG. 1C illustrates a fourth step in which a metal cover 13 is placed on the metal surround 11.

FIG. 1D illustrates a fifth step of the method, in which step a second hermetically sealed joint 14 is formed at the interface between the metal surround 11 and the cover 13, or alternatively between an upper face 111 of the surround 11 and the cover 13.

This second joint 14 is formed using a welding method involving a localized application of heat, such as laser welding.

In practice, using such a method, it proves to be difficult to reduce the thickness of the metal surround to a thickness of less than 1 mm.

This is because there are two problems that may occur below this value.

First of all, when the first hermetically sealed joint 12 is being formed by brazing, chemical elements contained in the brazed joint 12 diffuse through the thickness of the metal surround 11, resulting in undesirable attachment of the upper face 111 of the metal surround 11 to the holder. What happens is that the latter (not depicted in FIG. 1) is used to apply pressure to the upper face 111 of the metal surround 11 while the first hermetically sealed joint 12 is being formed.

For example, in instances in which the metal surround 11 is made of titanium and in which the first hermetically sealed joint 12 consists of titanium and nickel, during the braze annealing, the nickel diffuses through the thickness of the metal surround 11 and contributes to the creation of an undesirable region of attachment between the upper face 111 of the metal surround 11 and the holder.

In addition, during the formation of the second hermetically sealed joint 14 by laser welding, the first hermetically sealed joint 12 may be adversely heat-affected.

Reference will now be made to FIG. 2 which illustrates a method of manufacture of a hermetically sealed casing according to the invention.

FIG. 2A illustrates the first two steps of the method which are identical to the first two steps of the method according to the prior art.

They consist in supplying a ceramic substrate 20 and a metal surround 21 and in placing the latter so that it faces the substrate 20.

The ceramic substrate 20 may be made of alumina, zirconia, yttria-stabilized zirconia, or ceria-stabilized zirconia.

Advantageously, the ceramic substrate 20 has a surface area of between 10 mm$^2$ and 100 cm$^2$ and a thickness of between 10 μm and 1 mm, preferably between 10 μm and 100 μm.

The metal surround 21 may be made of titanium or titanium alloy. Advantageously, the metal surround 21 has a width of between 1 mm and 1 cm and a thickness of between 10 μm and 1 mm and, for preference, between 10 μm and 100 μm.

FIG. 2B illustrates another step in the method, in which a ceramic surround 25 is placed on the upper face 211 of the surround 21, which face is the opposite face to the interface between the metal surround 25 and the substrate 20.

Moreover, this ceramic surround 25 only partially covers the upper face 211 of the surround 21.

In the example illustrated in FIG. 2C, the surround 25 is situated on the same side as the inner face 213 of the metal surround 21.

More specifically, the interior edge 251 of the surround 25 is, in this example, situated substantially in vertical alignment above the interior face 213 of the metal surround 21.

The ceramic surround 25 may be made of alumina, zirconia, yttria-stabilized zirconia or ceria-stabilized zirconia.

Advantageously, the ceramic surround 25 has a width of between 1 mm and 1 cm and a thickness of between 10 μm and 1 mm, preferably, between 10 μm and 100 μm.

FIG. 2C illustrates the next step in which a first hermetically sealed joint 22 is formed at the interface between the substrate 20 and the metal surround 21, namely between the lower face 210 of the surround 21, which is the opposite face to the upper face 211, and the substrate 20.

This joint 22 is formed on a portion of the interface which faces the ceramic surround 25. This portion is therefore also situated towards the inside of the casing in the process of being produced.

Thus, when considering a plane of projection, common to the surround 25 and to the joint 22, for example the plane of the substrate 20, the projected surface of the surround 25 in this plane of projection is at least equal to the projected surface of the first hermetically sealed joint 22 in this same plane of projection. In addition, the relative position of the surround 25 and of the joint 22 is such that the projected surface of the surround 25 completely covers the projected surface of the joint 22.

Under no circumstances is the joint 22 formed on the entirety of the interface.

In general, the percentage of the surface area of the interface that is occupied by the joint 22 is between 20 and 80% so as to allow both effective assembly and the fitting of a cover.

This first hermetically sealed joint 22 may consist of titanium and of nickel.

During the formation of the first hermetically sealed joint 22, a region of attachment 220 is simultaneously formed between the upper face 211 of the metal surround 21 and the ceramic surround 25. What actually happens is that this is the result of the diffusion of the chemical elements contained in the brazed joint 22 through the thickness of the metal surround 21.

The ceramic surround 25 itself does not attach to the holder (which has not been depicted in FIG. 2) which is used to apply pressure to the ceramic surround 25, and therefore indirectly to the upper face 211 of the metal surround 21 during formation of the first hermetically sealed joint 22.

For example, in instances in which the metal surround is made of titanium and the first hermetically sealed joint 22 is made of titanium and of nickel, during the braze annealing, the nickel diffuses through the thickness of the metal surround 21 and contributes to forming the region of attachment 220 between the upper face 211 of the metal surround 21 and the ceramic surround 25. At the start of the braze annealing, the nickel is present only at the first hermetically sealed joint 22. However, at the end of the braze annealing, the nickel is present also at the region of attachment 220, and throughout that part of the metal surround 21 which is comprised between the first hermetically sealed joint 22 and the attachment region 220.

Thus, at the end of the braze annealing, three zones (first hermetically sealed joint 22, attachment region 220, and part of the metal surround 21 situated between the joint 22 and the attachment region 220) have a similar chemical composition, these three zones containing titanium and nickel.

FIG. 2D illustrates the next step in the method, in which step a metal cover 23 is placed on the upper face 211 of the metal surround 21.

In the embodiment illustrated in FIG. 2D, the outer edge 230 of the cover 23 is substantially in vertical alignment above the exterior face 212 of the metal surround 21, which is the opposite face to the interior surface 213.

Thus, the ceramic surround 25 is situated on the inside of the cavity 30 of the casing in the process of being formed.

The metal cover 23 may be made of titanium or titanium alloy.

Advantageously, the metal cover 23 has a thickness of between 10 μm and 1 mm, and preferably between 10 μm and 100 μm.

In a final step in the carrying-out of the method illustrated in FIG. 2E, a second hermetically sealed joint 24 is formed between the upper face 211 of the metal surround 21 and the cover 23.

This joint 24 is formed by a laser process carried out with a localized application of heat, such as laser welding.

During the formation of the second hermetically sealed joint 24, the risk of adversely heat-affecting the first hermetically sealed joint 22 is very low because the second hermetically sealed joint 24 is laterally offset from the first hermetically sealed joint 22, the first joint 22 being situated on the inside of the cavity 30 and the second joint 24 at the periphery of the cavity.

Thus, the two joints 22 and 24 are offset both in a common plane of projection parallel to the substrate 20 and in another common plane of projection perpendicular to the substrate 20.

The method illustrated in FIGS. 2A to 2E allows the creation of a slender hermetically sealed casing incorporating a metal surround, the thickness of which can be small, with no negative impact on the production method. In particular, the presence of the ceramic surround makes it possible to avoid any attachment of a holder to the metal surround, despite the small thickness of this surround.

In addition, the lateral offset between the two hermetically sealed joints means that any impairing of the first hermetically sealed joint when creating the second joint can be avoided.

Reference is now made to FIG. 3 which illustrates an alternative form of embodiment of the method illustrated in FIG. 2.

As illustrated in FIG. 3A, this alternative form of embodiment involves arranging the ceramic surround 25 on the outside of the metal surround 21 so as to partially cover the upper face 211 of the surround 21.

Thus, in the example illustrated in FIG. 3A, the outer edge 250 of the ceramic surround 25, which is the opposite edge to the interior edge 251, is situated substantially in vertical alignment above the exterior face 212 of the metal surround 21, which is the opposite face to the interior face 213.

The first hermetically sealed joint 22 is formed at the interface between the metal surround 21 and the substrate 20 as described previously with reference to FIG. 2C and this process will not be described again in detail.

This step makes it possible not only to obtain the hermetically sealed joint 22 between the lower face 210 of the surround 21 and the substrate 20 but also a region of attachment 220 between the upper face 211 of the surround 21 and the ceramic surround 25.

As in the method illustrated in FIG. 2, the projected surface of the ceramic surround 25 in a plane of projection is at least equal to the projected surface of the joint 22 in this same plane. This common plane of projection may notably comprise the joint 22 and correspond to the plane of the substrate 20.

In addition, the relative position of the ceramic surround 25 and of the joint 22 is such that the projected surface of the surround 25 completely covers the projected surface of the joint 22 in this common plane of projection.

Thus, the surround 25 avoids any attachment of a holder to the metal surround 21.

The cover 33 is then superposed on the assembly obtained.

FIG. 3B shows that, in this alternative form of embodiment of the method, the exterior edge 330 of the cover 33 is situated towards the inside of the casing in the process of being produced with respect to the ceramic surround 25.

The final step in the method consists in forming the second hermetically sealed joint 24, as was described with reference to FIG. 2E.

FIG. 3B shows the casing thus obtained.

Unlike in the casing illustrated in FIG. 2E, the ceramic surround 25 here is situated on the outside of the cavity 40 formed by the casing.

This second alternative form of embodiment of the method offers the same advantages as those described with reference to the method described with reference to FIG. 2.

Here again, the lateral offset between the two hermetically sealed joints makes it possible to avoid any impairment of the first hermetically sealed joint 22 during creation of the second joint 24.

This is because the first joint 22 is situated on the outside of the cavity 40 whereas the second joint is situated at the periphery of this cavity.

Another alternative form of the method according to the invention is to create a recess in the ceramic substrate 20, in which recess the brazed joint 22 is formed, the joint being at least partially incorporated into this recess.

Another alternative form of the method is to provide such a recess in the metal surround 21.

It is also possible to combine these two alternative forms by providing a recess both in the ceramic substrate 20 and in the metal surround 21.

In all three instances, the presence of this recess allows the thickness of the hermetic casing obtained by the method according to the invention to be reduced still further because the brazed joint is situated partially in the recess created in the substrate and/or the cover. Indeed the impact that the thickness of the brazed joint has on the thickness of the casing is thus reduced.

The reference signs inserted after the technical features featured in the claims are intended solely to make the latter easier to understand and do not in any way restrict the scope thereof.

The invention claimed is:

1. Method for producing a hermetically sealed casing, comprising the following steps:
   a) supplying a ceramic substrate (20),
   b) supplying a metal surround (21) and placing it facing the said substrate (20),
   c) forming a first hermetically sealed joint (22) at the interface between the said substrate (20) and the said metal surround (21), in order to assemble them and form an assembly, d) superposing a cover (23, 33) on the said assembly, e) forming a second hermetically sealed joint (24) between an upper face (211) of the metal surround (21) which is the opposite face to the said interface, and the cover (23, 33), in order to obtain the said casing, characterized in that, during step c), the first hermetically sealed joint (22) is formed on a portion of the said interface and in that prior to step c), the method involves an additional step consisting in placing a ceramic surround (25) on the upper face (211) of the metal surround so as to partially cover the said face of the metal surround, the ceramic surround has a projected surface defining a plane of projection, the said plane of projection covering a projected surface of the said first joint.

2. Method according to claim 1, characterized in that the first hermetically sealed joint (22) formed during step c) is a brazed joint.

3. Method according to claim 2, characterized in that, during step a), a substrate in which a recess is formed is supplied, the brazed joint being incorporated at least partially into the said recess.

4. Method according to claim 2, characterized in that, during step b), a metal surround in which a recess is formed is supplied, the brazed joint being at least partially incorporated into the said recess.

5. Method of encapsulating a device consisting in implementing the method according to claim 1 and in mounting at least one component of the said device that is to be encapsulated on the said substrate (20), after step c).

6. Hermetically sealed casing comprising:

a ceramic substrate (20), a metal surround (21) hermetically connected to the substrate by a first joint (22) situated on a portion of the interface between the said substrate (20) and the said surround (21), and a cover (23, 33) hermetically connected to the a cover (23, 33) hermetically connected to the said metal surround (21) by a second hermetically sealed joint (24), so as to define a cavity (30, 40), characterized in that a ceramic surround (25) is connected to the said metal surround (21) on an opposite face (211) to the said interface, so as to partially cover the said face (211) of the metal surround, the ceramic surround has a projected surface defining a plane of projection, the said plane of projection covering a projected surface of the said first joint.

7. Casing according to claim 6, characterized in that the surround (25) is situated on the inside of the cavity (30).

8. Casing according to claim 6, characterized in that the ceramic surround (25) is situated on the outside of the cavity (40).

9. Casing according to claim 6, characterized in that the first hermetically sealed joint (22) is a brazed joint.

10. Casing according claim 6, characterized in that the said substrate (20) and/or the said metal surround (21) comprises a recess into which the first hermetically sealed joint is at least partially incorporated.

* * * * *